(12) United States Patent
Chen et al.

(10) Patent No.: US 8,308,799 B2
(45) Date of Patent: Nov. 13, 2012

(54) MODULAR INTRAOCULAR LENS INJECTOR DEVICE

(75) Inventors: Bill Chen, Irvine, CA (US); James Y. Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 396 days.

(21) Appl. No.: 12/763,322

(22) Filed: Apr. 20, 2010

(65) Prior Publication Data

US 2011/0257658 A1    Oct. 20, 2011

(51) Int. Cl.
    *A61F 9/007*    (2006.01)
(52) U.S. Cl. ...................... 623/6.12; 606/107
(58) Field of Classification Search ................. 623/6.12; 606/107
    See application file for complete search history.

(56) References Cited

U.S. PATENT DOCUMENTS

| | | |
|---|---|---|
| 4,573,998 A | 3/1986 | Mazzocco |
| 4,619,657 A | 10/1986 | Keates et al. |
| 4,681,102 A | 7/1987 | Bartell |
| 4,747,404 A | 5/1988 | Jampel et al. |
| 4,834,094 A | 5/1989 | Patton et al. |
| 4,836,201 A | 6/1989 | Patton et al. |
| 4,919,130 A | 4/1990 | Stoy et al. |
| 4,934,363 A | 6/1990 | Smith et al. |
| 4,960,557 A | 10/1990 | Sorensen |
| 5,007,913 A | 4/1991 | Dulebohn et al. |
| 5,026,396 A | 6/1991 | Darin |
| 5,098,439 A | 3/1992 | Hill et al. |
| 5,190,552 A | 3/1993 | Kelman |
| 5,275,604 A | 1/1994 | Rheinish et al. |
| 5,304,182 A | 4/1994 | Rheinish et al. |
| 5,354,333 A | 10/1994 | Kammann et al. |
| 5,397,313 A | 3/1995 | Gross |
| 5,425,734 A | 6/1995 | Blake |
| 5,444,183 A | 8/1995 | Gehrs et al. |
| 5,464,396 A | 11/1995 | Barta et al. |
| 5,468,246 A | 11/1995 | Blake |
| 5,494,484 A | 2/1996 | Feingold |
| 5,496,278 A | 3/1996 | Buff |
| 5,496,328 A | 3/1996 | Nakajima et al. |

(Continued)

FOREIGN PATENT DOCUMENTS

AU    728443    1/2001

(Continued)

OTHER PUBLICATIONS

International Search Report for PCT/US2011/032708, Publication No. WO2011/133427, 2 pages.

(Continued)

*Primary Examiner* — Ryan Severson
(74) *Attorney, Agent, or Firm* — Darien Reddick

(57) ABSTRACT

An intraocular lens (IOL) injection device is modularized to enable cleaning of internal components after surgery. The device includes first and second housing modules. These modules collectively define a passageway along which an injector rod moves between a retracted position and an extended position. The first module is further configured to accommodate a lens cartridge module. The cartridge module has disposed therein an IOL, in alignment with the passageway. Thus as the rod moves from the retracted position to the extended position, a front portion of the rod that is substantially surrounded by the first module in the retracted position moves into the cartridge module and displaces the IOL. This causes the front portion of the rod to accumulate on it viscoelastic substances. The first module, though, is configured to detach from the second module, to thereby expose the front portion of the rod in the retracted position for cleaning.

14 Claims, 9 Drawing Sheets

U.S. PATENT DOCUMENTS

| | | | |
|---|---|---|---|
| 5,499,987 | A | 3/1996 | Feingold |
| 5,578,042 | A | 11/1996 | Cumming |
| 5,582,614 | A | 12/1996 | Feingold |
| 5,607,433 | A | 3/1997 | Polla et al. |
| 5,616,148 | A | 4/1997 | Eagles et al. |
| 5,620,450 | A | 4/1997 | Eagles et al. |
| 5,629,577 | A | 5/1997 | Polla et al. |
| 5,643,275 | A | 7/1997 | Blake |
| 5,643,276 | A | 7/1997 | Zaleski |
| 5,653,715 | A | 8/1997 | Reich et al. |
| 5,653,753 | A | 8/1997 | Brady et al. |
| 5,716,364 | A | 2/1998 | Makker et al. |
| 5,728,102 | A | 3/1998 | Feingold et al. |
| 5,735,858 | A | 4/1998 | Makker et al. |
| 5,772,666 | A | 6/1998 | Feingold et al. |
| 5,776,138 | A | 7/1998 | Vidal et al. |
| 5,800,441 | A | 9/1998 | Polla et al. |
| 5,800,442 | A | 9/1998 | Wolf et al. |
| 5,803,925 | A | 9/1998 | Yang et al. |
| 5,810,834 | A | 9/1998 | Heyman |
| 5,820,373 | A | 10/1998 | Okano et al. |
| 5,860,986 | A | 1/1999 | Reich et al. |
| 5,868,752 | A | 2/1999 | Makker et al. |
| 5,873,879 | A | 2/1999 | Figueroa et al. |
| 5,876,406 | A | 3/1999 | Wolf et al. |
| 5,876,407 | A | 3/1999 | Makker et al. |
| 5,891,153 | A | 4/1999 | Peterson |
| 5,944,725 | A | 8/1999 | Cicenas et al. |
| 5,947,976 | A | 9/1999 | Van Noy et al. |
| 6,010,510 | A | 1/2000 | Brown et al. |
| 6,042,587 | A | 3/2000 | Polla et al. |
| 6,056,758 | A | 5/2000 | Vidal et al. |
| 6,083,231 | A | 7/2000 | Van Noy et al. |
| 6,140,602 | A | 10/2000 | Costin |
| 6,143,001 | A | 11/2000 | Brown et al. |
| 6,162,229 | A | 12/2000 | Feingold et al. |
| 6,162,230 | A | 12/2000 | Polla et al. |
| 6,179,843 | B1 | 1/2001 | Weiler |
| 6,228,094 | B1 | 5/2001 | Erdman |
| 6,254,607 | B1 | 7/2001 | Makker et al. |
| 6,334,862 | B1 | 1/2002 | Vidal et al. |
| 6,355,046 | B2 | 3/2002 | Kikuchi et al. |
| 6,423,035 | B1 | 7/2002 | Das et al. |
| 6,447,519 | B1 | 9/2002 | Brady et al. |
| 6,471,708 | B2 | 10/2002 | Green |
| 6,497,708 | B1 | 12/2002 | Cumming |
| 6,500,181 | B1 | 12/2002 | Portney |
| 6,503,275 | B1 | 1/2003 | Cumming |
| 6,558,395 | B2 | 5/2003 | Hjertman et al. |
| 6,592,591 | B2 | 7/2003 | Polla et al. |
| 6,607,537 | B1 | 8/2003 | Binder |
| 6,635,731 | B2 | 10/2003 | Mentak |
| 6,666,871 | B2 | 12/2003 | Klkuchi et al. |
| 6,685,740 | B2 | 2/2004 | Figueroa et al. |
| 6,899,717 | B2 | 5/2005 | Weber et al. |
| 6,923,815 | B2 | 8/2005 | Brady et al. |
| 6,964,648 | B2 | 11/2005 | Talling et al. |
| 6,976,989 | B1 | 12/2005 | Vincent |
| 7,014,641 | B2 | 3/2006 | Kobayshi et al. |
| 7,042,180 | B2 | 5/2006 | Terry et al. |
| 7,131,976 | B2 | 11/2006 | Kobayashi et al. |
| 7,156,854 | B2 | 1/2007 | Brown et al. |
| 7,156,855 | B2 | 1/2007 | Oda |
| 7,189,218 | B2 | 3/2007 | Lichtenberg |
| 7,279,006 | B2 | 10/2007 | Vincent |
| 7,422,604 | B2 | 9/2008 | Vaquero et al. |
| 7,429,263 | B2 | 9/2008 | Vaquero et al. |
| 2001/0007075 | A1 | 7/2001 | Hjertman et al. |
| 2003/0040755 | A1 | 2/2003 | Meyer |
| 2003/0135221 | A1 | 7/2003 | Sabet |
| 2003/0139749 | A1 | 7/2003 | Kikuchi et al. |
| 2003/0212406 | A1 | 11/2003 | Kobayashi et al. |
| 2003/0212409 | A1 | 11/2003 | Kobayashi et al. |
| 2004/0054374 | A1 | 3/2004 | Weber et al. |
| 2004/0087896 | A1 | 5/2004 | Wise et al. |
| 2004/0097956 | A1 | 5/2004 | Oda |
| 2004/0147938 | A1 | 7/2004 | Dusek et al. |
| 2004/0160575 | A1 | 8/2004 | Ayton et al. |
| 2004/0199174 | A1 | 10/2004 | Herberger et al. |
| 2004/0215207 | A1 | 10/2004 | Cumming |
| 2004/0238392 | A1 | 12/2004 | Peterson et al. |
| 2005/0049605 | A1 | 3/2005 | Vaquero et al. |
| 2005/0049606 | A1 | 3/2005 | Vaquero et al. |
| 2005/0065534 | A1 | 3/2005 | Hohl |
| 2005/0143750 | A1 | 6/2005 | Vaquero |
| 2005/0149056 | A1 | 7/2005 | Rathert |
| 2005/0203619 | A1 | 9/2005 | Altmann |
| 2005/0222578 | A1 | 10/2005 | Vaquero |
| 2005/0222579 | A1 | 10/2005 | Vaquero et al. |
| 2006/0066962 | A1 | 3/2006 | Totzeck et al. |
| 2006/0085013 | A1 | 4/2006 | Dusek et al. |
| 2006/0167466 | A1 | 7/2006 | Dusek |
| 2006/0184181 | A1 | 8/2006 | Cole et al. |
| 2006/0200167 | A1 | 9/2006 | Peterson et al. |
| 2006/0229633 | A1 | 10/2006 | Shepherd |
| 2006/0229634 | A1 | 10/2006 | Shepherd |
| 2006/0235429 | A1 | 10/2006 | Lee et al. |
| 2006/0284581 | A1 | 12/2006 | Mullin et al. |
| 2007/0005135 | A1 | 1/2007 | Makker et al. |
| 2007/0050023 | A1 | 3/2007 | Bessiere et al. |
| 2007/0060925 | A1 | 3/2007 | Pynson |
| 2007/0150056 | A1 | 6/2007 | Meyer |
| 2007/0173860 | A1 | 7/2007 | Iwaski |
| 2008/0033449 | A1 | 2/2008 | Cole et al. |
| 2008/0039862 | A1 | 2/2008 | Tran |
| 2008/0058830 | A1 | 3/2008 | Cole et al. |
| 2008/0097459 | A1 | 4/2008 | Kammerlander et al. |
| 2008/0119865 | A1 | 5/2008 | Meunier et al. |
| 2008/0200920 | A1 | 8/2008 | Downer |
| 2008/0200921 | A1 | 8/2008 | Downer |
| 2008/0221584 | A1 | 9/2008 | Downer |
| 2008/0221585 | A1 | 9/2008 | Downer |
| 2008/0255577 | A1 | 10/2008 | Downer |
| 2009/0043313 | A1 | 2/2009 | Ichinohe et al. |
| 2009/0112223 | A1 | 4/2009 | Downer |
| 2009/0171366 | A1 | 7/2009 | Tanaka |
| 2009/0204123 | A1 | 8/2009 | Downer |
| 2009/0216244 | A1 | 8/2009 | Pynson |

FOREIGN PATENT DOCUMENTS

| | | |
|---|---|---|
| DE | 4301573 | 7/1994 |
| EP | 0174917 | 3/1986 |
| EP | 0270 257 | 6/1988 |
| EP | 0363 213 | 4/1990 |
| EP | 0477466 | 6/1996 |
| EP | 0858304 | 8/1998 |
| EP | 0962195 | 12/1999 |
| EP | 1011 561 | 6/2000 |
| EP | 1076 408 | 2/2001 |
| EP | 1 332 731 A1 | 8/2003 |
| EP | 1 332 731 B1 | 8/2003 |
| EP | 1360944 | 11/2003 |
| EP | 1481652 | 12/2004 |
| EP | 1661533 | 5/2006 |
| EP | 1849436 A1 | 10/2007 |
| EP | 1891911 | 2/2008 |
| EP | 1958593 | 8/2008 |
| EP | 2062552 | 5/2009 |
| FR | 2820633 | 8/2002 |
| GB | 2 224 214 | 5/1990 |
| JP | 1176288 | 12/1989 |
| JP | 10309294 | 11/1998 |
| JP | 10511876 | 11/1998 |
| JP | 10512460 | 12/1998 |
| JP | 2000-025073 | 1/2000 |
| JP | 2003070829 | 3/2003 |
| JP | 2003325569 | 11/2003 |
| JP | 2006-014962 | 1/2006 |
| JP | 2006181269 | 7/2006 |
| JP | 2007-055057 | 3/2007 |
| RU | 2138232 | 9/1999 |
| RU | 2171100 | 7/2001 |
| RU | 2238283 | 10/2004 |
| RU | 2242956 | 12/2004 |
| SU | 1440496 | 11/1988 |
| WO | WO 9407436 A1 | 4/1994 |
| WO | WO 94/20027 | 9/1994 |

| WO | WO 96/10372 | 4/1996 |
| WO | WO 96/20662 | 7/1996 |
| WO | WO 96/28122 | 9/1996 |
| WO | WO 96/29956 | 10/1996 |
| WO | WO 97/15253 | 5/1997 |
| WO | WO 97/26841 | 7/1997 |
| WO | WO 98/05281 | 2/1998 |
| WO | WO 98/12969 | 4/1998 |
| WO | WO 98/15244 | 4/1998 |
| WO | WO 98/20819 | 5/1998 |
| WO | WO 00/40175 | 7/2000 |
| WO | WO 00/62712 | 10/2000 |
| WO | WO 2004/091447 | 10/2004 |
| WO | WO 2005/018515 | 3/2005 |
| WO | WO 2005/020853 | 3/2005 |
| WO | WO 2005/023154 A2 | 3/2005 |
| WO | WO 2005/023154 A3 | 3/2005 |
| WO | WO 2005/102223 | 11/2005 |
| WO | WO 2006/059183 | 6/2006 |
| WO | WO 2006/070561 | 7/2006 |
| WO | WO 2006/080191 | 8/2006 |
| WO | WO 2006/113138 | 10/2006 |
| WO | WO 2006/113357 | 10/2006 |

OTHER PUBLICATIONS

Written Opinion of the International Searching Authority, International Application No. PCT/US2011/032708, Jun. 29, 2011, 4 pages.

European Search Report for Application No. 08102172.7, Publication No. 1980219, dated Oct. 15, 2008, 5 pages.

International Search Report for PCT/US2009/057,083, Publication No. WO2010/044,974, 5 pages.

Written Opinion of the International Searching Authority, International Application No. PCT/US2009/057,083, Dec. 30, 2009, 6 pages.

Abstract of article entitled "Implantation of the AcrySof MA30BA lens using the Monarch System" by Barakova D., original article found in Cesk slov Oftalmol, 2002 58(3), at p. 149-152, found in PubMed database at http://www.ncbi.nlm.nih.gov/pubmed/12087658 (1 page).

International Preliminary Report on Patentability, PCT/US2009/057083, Apr. 19, 2011, 1 page.

International Search Report for PCT/US2010/023544, Publication No. WO2010/093593, 4 pages.

PCT International Preliminary Report on Patentability and Written Opinion, PCT/US2010/023544, Aug. 16, 2011, 4 pages.

European Search Report for Application No. 07114085.9, Publication No. EP1891911, dated Jan. 14, 2008, 2 pages.

European Search Report for Application No. 08100876.5, Publication No. EP1958593, dated Apr. 22, 2008, 2 pages.

European Search Report for Application No. 09154535.0, Publication No. EP2062552, dated Apr. 15, 2009, 2 pages.

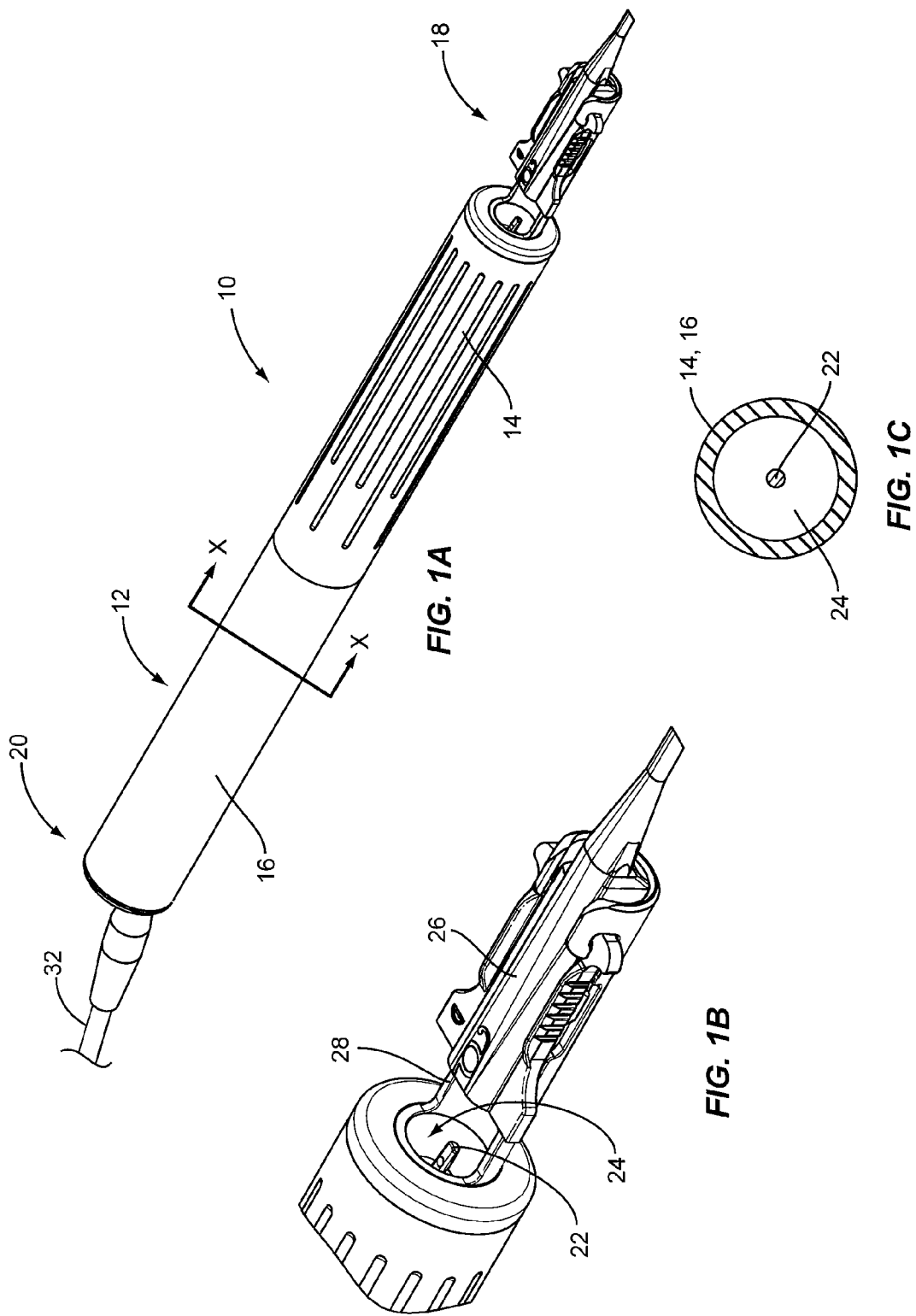

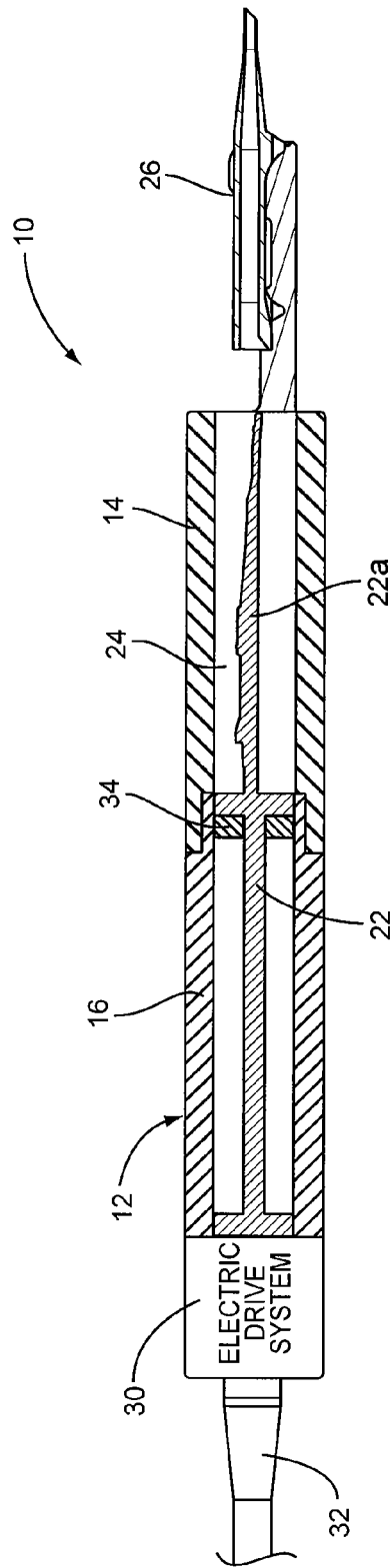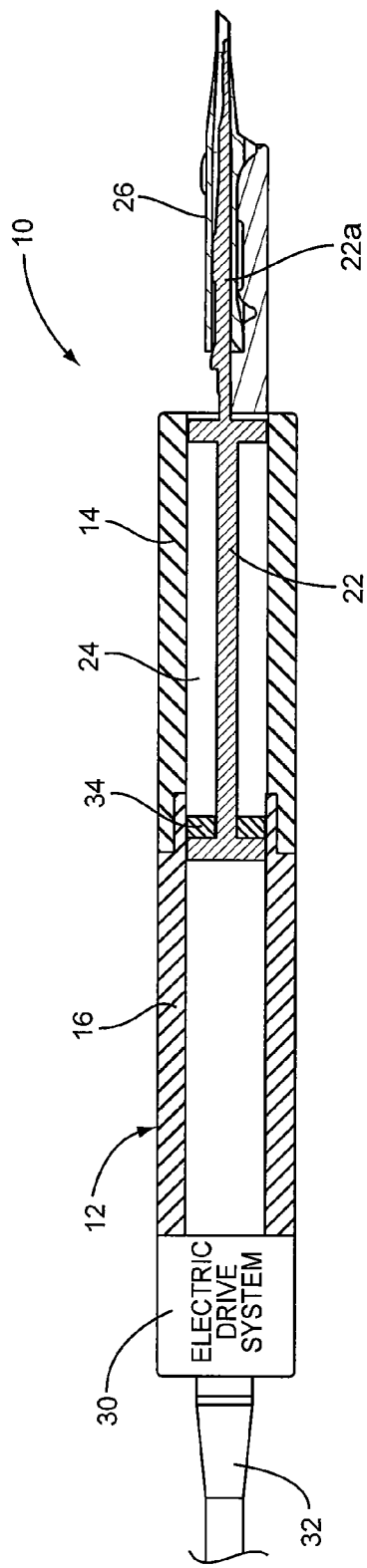
FIG. 2A
FIG. 2B

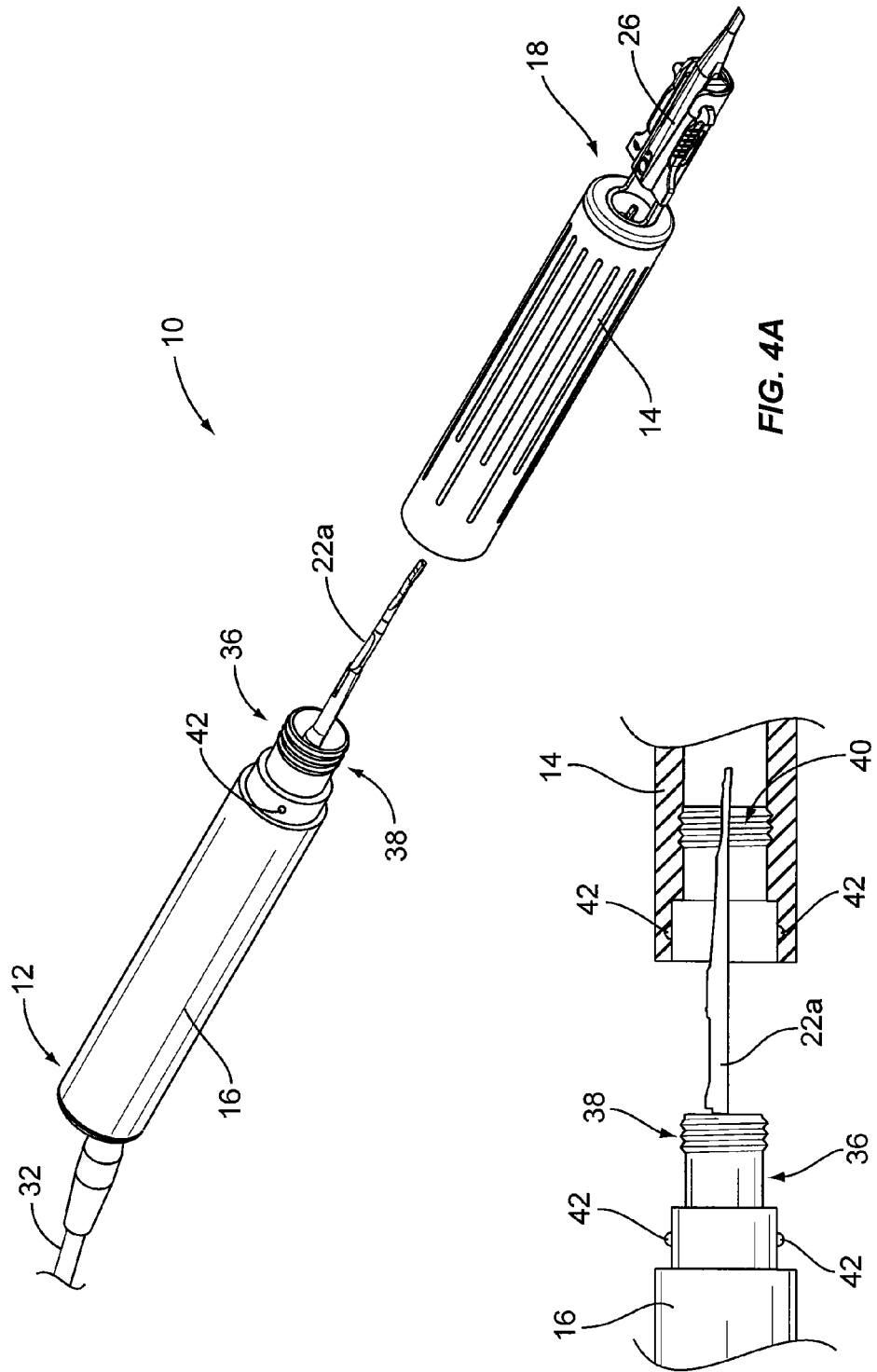

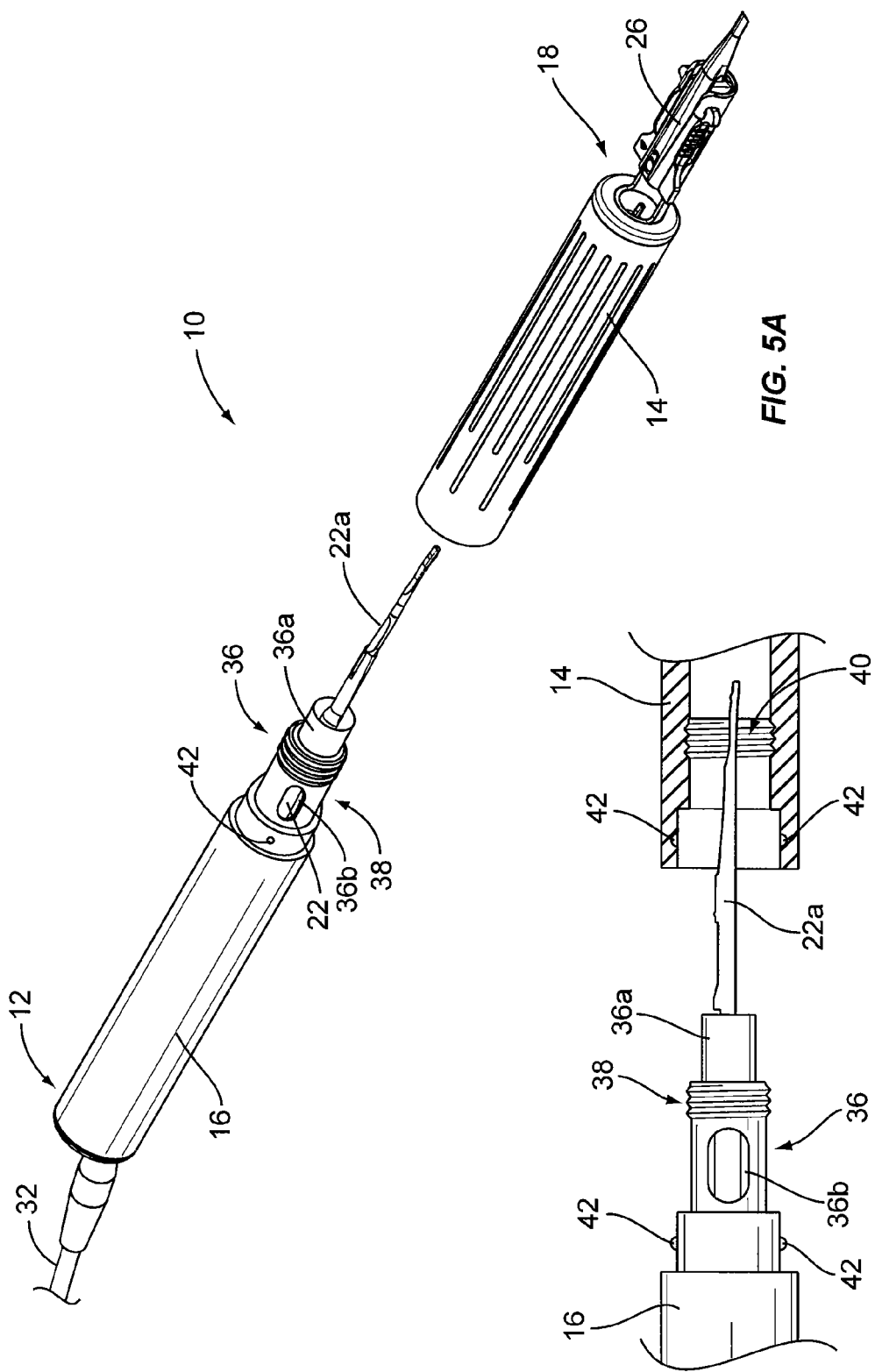

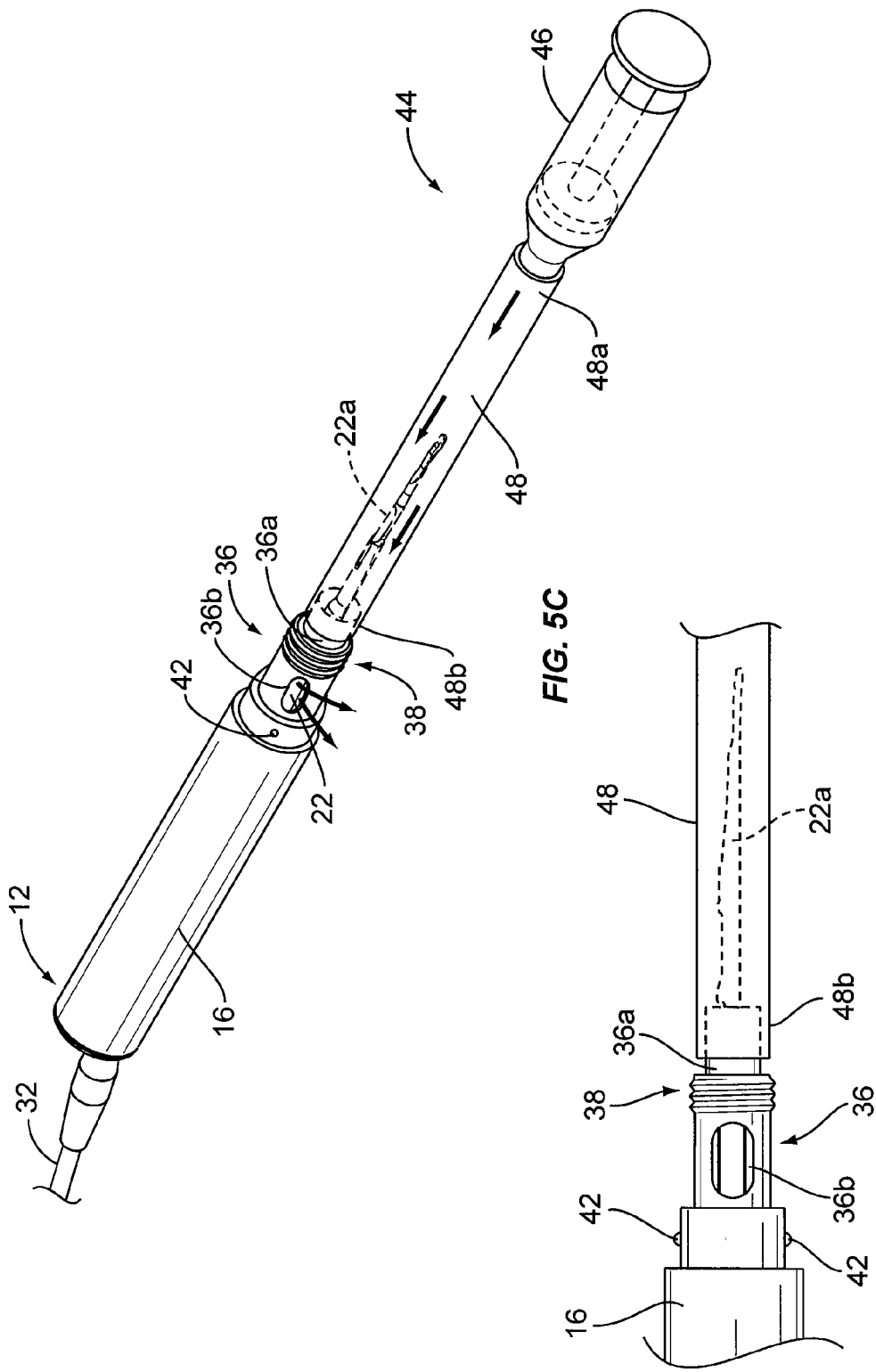

MODULAR INTRAOCULAR LENS INJECTOR DEVICE

TECHNICAL FIELD

The present invention relates generally to an intraocular lens injector device for surgically injecting an intraocular lens into an eye, and more particularly to an intraocular lens injector device that is modularized to enable cleaning of internal components after surgery.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the eye's natural lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial IOL.

An IOL injector device injects the artificial IOL into the eye through the same small incision used to remove the diseased lens. The IOL injector device typically includes a tubular housing with an injector rod disposed therein and a lens cartridge that contains the artificial IOL. With the tip of the lens cartridge inserted into the incision, the IOL injector device physically translates the injector rod toward the lens cartridge, thereby displacing the artificial IOL from the lens cartridge and into the eye.

During surgery, substances often accumulate on the internal components of the IOL injector device, including for example the injector rod. For instance, viscoelastic substances (e.g., Ophthalmic Viscoelastic Devices, OVD), which have both high viscosity and elasticity, are widely utilized in cataract surgery to create and reserve space for, or to coat, the artificial IOL. Accordingly, when the injector rod displaces the artificial IOL from the lens cartridge, viscoelastic substances unavoidably accumulate on the surface of the rod. If the injector rod is not re-processed (i.e., cleaned) to remove the accumulated viscoelastic substances, the substances can contaminate and introduce complications to subsequent patients undergoing cataract surgery with the same device.

SUMMARY

Teachings herein include a device for injecting an intraocular lens (IOL) into the lens capsule of an eye. The device is modularized to enable cleaning of internal components, such as an injector rod, after surgery.

According to an exemplary embodiment, an IOL injection device includes a tubular housing that comprises a first module and a second module. The first module is disposed at a front end of the housing and the second module is disposed posterior to the first module, e.g., at a rear end of the housing. These modules collectively define a passageway that extends from the second module, through the first module, to the front end of the housing. An injector rod is longitudinally disposed within and moveable along this passageway.

The first module is further configured to accommodate a lens cartridge module at or near the front end of the housing. The lens cartridge module has disposed therein an IOL, in alignment with the passageway defined by the first and second modules. Aligned with the passageway, the IOL is displaced from the lens cartridge module by the injector rod as the rod moves along the passageway and into the lens cartridge module.

More particularly, the injector rod moves along the passageway over an operating range between a retracted position and an extended position. A front portion of the injector rod remains substantially surrounded by the first module in the retracted position. As the injector rod moves from the retracted position to the extended position, though, this front portion of the rod moves into the cartridge module and displaces the IOL therefrom.

When the IOL is injected into the eye in this way, substances used during surgery (e.g., viscoelastic substances) accumulate on the internal components of the IOL injector device, especially the front portion of the injector rod. To enable cleaning of these internal components, the first module is configured to detach from the second module, to thereby expose the front portion of the injection rod in the retracted position for cleaning. Once the front portion of the injector rod is cleaned, the first and second modules may be configured to then reattach for surgical use.

In some circumstances of the device's surgical use, the internal components of the device, can be adequately cleaned of accumulated substances as described above. In other circumstance, however, the substances may also accumulate on those portions of the internal components not exposed by detaching the first and second modules as described. Accordingly, in other embodiments of the present invention, the second module is configured to, when not attached to the first module, removably attach to a cleaning module (e.g., a syringe filled with a balanced salt solution and a tube for injecting that solution). The cleaning module is configured to inject cleaning fluid onto various internal components of the device, e.g., the injector rod, including those portions not otherwise exposed when the injector rod is in the retracted position.

Of course, those skilled in the art will appreciate that the present invention is not limited to the above features, advantages, contexts or examples, and will recognize additional features and advantages upon reading the following detailed description and upon viewing the accompanying drawings.

BRIEF DESCRIPTION OF THE DRAWINGS

FIG. 1A is an isometric view of an exemplary IOL injection device, with a lens cartridge module installed.

FIG. 1B is a magnified view of the lens cartridge module and a first module of the exemplary IOL injection device illustrated in FIG. 1A.

FIG. 1C is a cross-sectional view of FIG. 1A, taken along line XX.

FIGS. 2A and 2B are cross-sectional views of an IOL injection device, respectively illustrating an injector rod in a retracted position and in an expanded position.

FIGS. 4A and 4B are respectively isometric and cross-sectional views of an IOL injection device with various attachment features for removably attaching the modules of the device, according to one embodiment of the present invention.

FIGS. 5A-5E are various views of an IOL injection device configured to removably attach to a cleaning module for cleaning, according to one embodiment of the present invention.

DETAILED DESCRIPTION

Figure 3A:
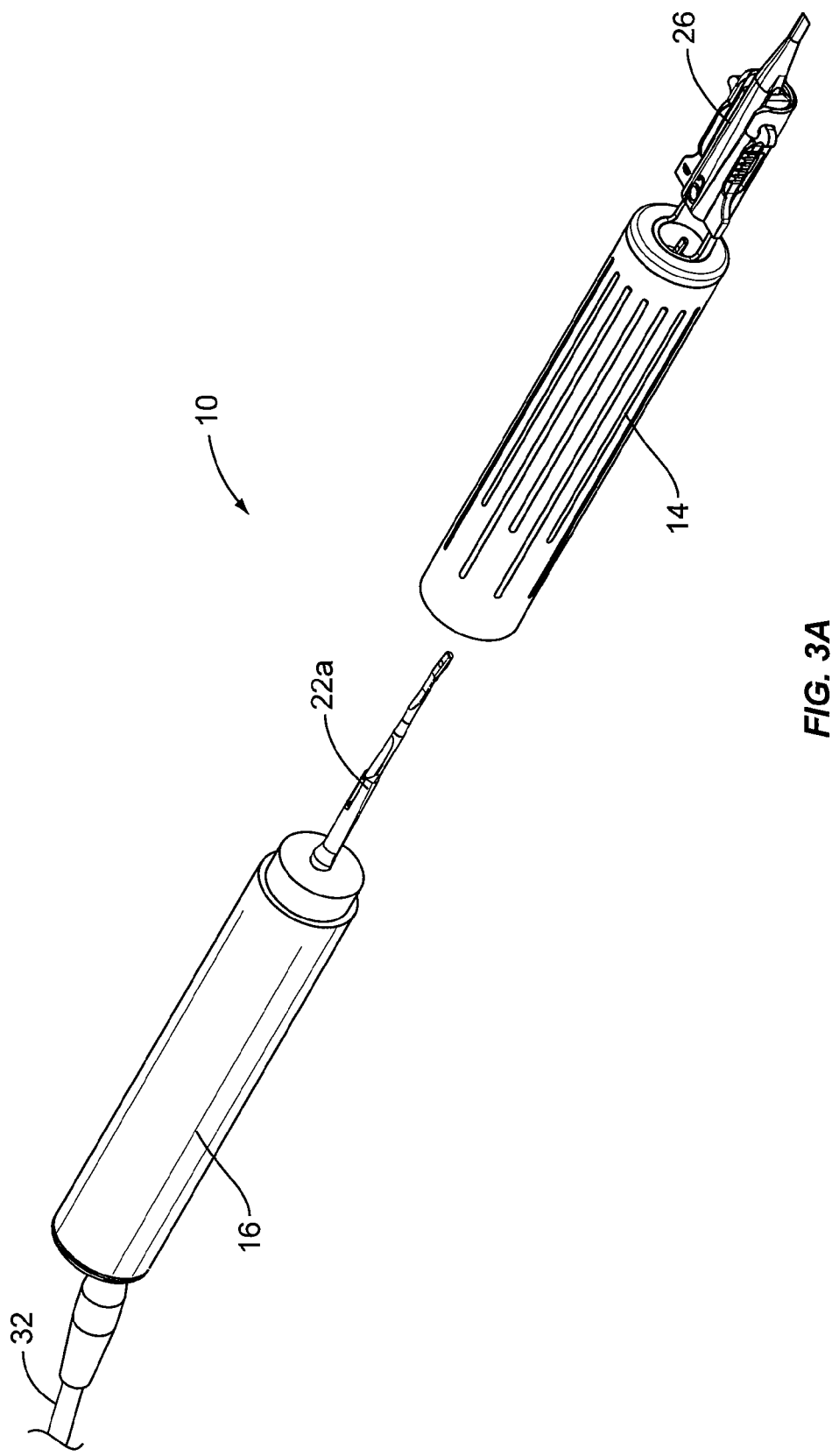
FIGS. 3A and 3B are respectively isometric and cross-sectional views of an IOL injection device modularized to enable cleaning of internal components after surgery, according to one embodiment of the present invention.

FIGS. 1A-1C illustrate a device 10 for injecting an artificial intraocular lens (IOL) into the anterior capsule of an eye. The IOL injection device 10 includes a tubular housing 12 that comprises a first module 14 and a second module 16. The first module 14 is disposed at a front end 18 of the housing 12 and the second module 16 is disposed posterior to the first module 14, e.g., at a rear end 20 of the housing 12.

The modules 14, 16 are configured to house therein various internal components of the IOL injection device 10. The modules 14, 16, for example, house an injector rod 22. More particularly, the modules 14, 16 collectively define a passageway 24 that extends from the second module 16, through the first module 14, to the front end 18 of the housing 12. The injector rod 22 is longitudinally disposed within and moveable along this passageway 24.

The first module 14 is further configured to accommodate a lens cartridge module 26 at or near the front end 18 of the housing 12. In some embodiments, for instance, the first module 14 includes a lens cartridge module mount 28 that is press-fitted to the front end 18 of the housing 12. This lens cartridge module mount 28 removably mounts the lens cartridge module 26 to the front end 18 of the housing 12, e.g., via a unique cutout configured to hold the lens cartridge module 26.

The lens cartridge module 26 has disposed therein an intraocular lens (IOL), in alignment with the passageway 24 defined by the modules 14, 16. Aligned with the passageway 24, the IOL is displaced from the lens cartridge module 26 by the injector rod 22 as the rod 22 moves along the passageway 24 and into the lens cartridge module 26.

Specifically, as shown in FIGS. 2A-2B, the injector rod 22 moves along the passageway 24 over an operating range between a retracted position (FIG. 2A) and an extended position (FIG. 2B). In some embodiments, an electric drive system 30 housed by the second module 30 and powered by a cable assembly 32 enables the injector rod 22 to move in this way. The electric drive system 30 may, for example, include an electric motor and be configured to cause longitudinal translation of the injector rod 22 along the passageway 24 over the operating range between the retracted position and the extended position. The movement of the injector rod 22 along the passageway 24 may be limited to the operating range between the retracted position and the extended position by one or more mechanical stops 34, by electrical control signals, or some combination of both.

Irrespective of the means by which the rod 22 is moved, a front portion 22a of the rod 22 remains substantially surrounded by the first module 14 in the retracted position. As the rod 22 moves from the retracted position to the extended position, the front portion 22a of the rod 22 moves into the lens cartridge module 26 and displaces the IOL therefrom and into the eye.

When the IOL is injected into the eye in this way, the internal components of the IOL injector device 10, especially the front portion 22a of the injector rod 22, may accumulate on them substances used during surgery (e.g., viscoelastic substances). If the injector rod 22 is not cleaned to remove the accumulated substances, the substances can contaminate and introduce complications to subsequent patients undergoing cataract surgery with the same device 10.

Figure 3B:
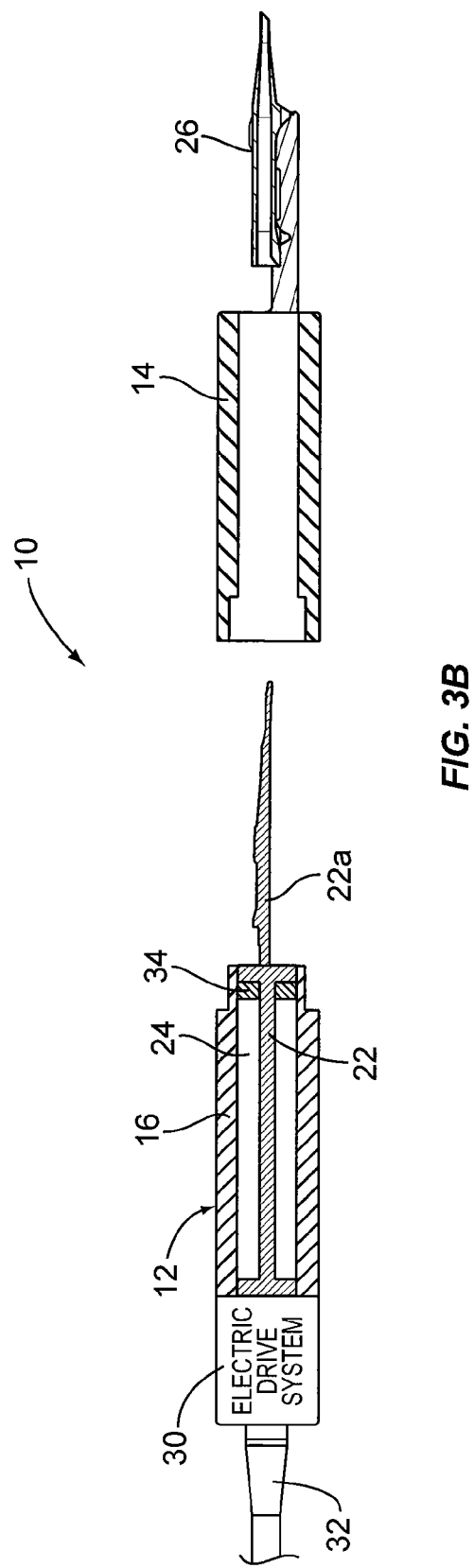

Accordingly, the device 10 is modularized as shown in FIGS. 3A-3B to enable cleaning of internal components like the injector rod 22 after surgery. As pictured, the first module 14 is configured to detach from the second module 16, to thereby expose the front portion 22a of the injector rod 22 in the retracted position for cleaning. Cleaning may simply entail wiping off the substances accumulated on the front portion 22a of the injector rod 22, or more thoroughly entail flushing, soaking, and ultrasonically sterilizing the front portion 22a of the injector rod 22. Once the front portion 22a of the injector rod 22 is cleaned, the first module 14 and the second module 16 may be configured to then reattach for surgical use.

In some embodiments, for example, the first module 14 includes a first attachment feature and the second module 16 includes a second attachment feature. These attachment features are configured to attach to one another, for surgical use, and to detach from one another, for cleaning. In one embodiment, the first and second attachment features are respective portions of a snap-fit mechanism that enables the first module 14 to snap onto the second module 16, and to likewise snap loose from the second module 16. In another embodiment, the first attachment feature comprises mechanical threads disposed on an interior surface of the first module 14, while the second attachment feature comprises mechanical threads disposed on an exterior surface of the second module 16. These mechanical threads are configured to engage with one another, to permit attachment and detachment of the first and second modules 14, 16. Yet another embodiment includes some combination of these snap-fit mechanisms and mechanical threads.

Consider, for example, the embodiments illustrated in FIGS. 4A-4B. In FIGS. 4A-4B, the second module 16 includes an injector rod sleeve 36 concentric therewith. The injector rod sleeve 36 protrudes from the second module 16, toward the front end 18 of the housing 12, in cantilever fashion, and surrounds at least a portion of the rod 22 longitudinally disposed therein. The injector rod sleeve 36 includes mechanical threads 38 disposed on an exterior surface thereof. These mechanical threads 38 are configured to engage mechanical threads 40 disposed on an interior surface of the first module 14. Additionally, the first and second modules 14, 16 include respective portions of one or more snap-fit mechanisms 42 that, when engaged, snap or secure the modules 14, 16 together. Accordingly, the modules 14, 16 are configured to attach together in these embodiments by the first module 14 overlapping and screwing onto the injector rod sleeve 36, via the mechanical threads 38, 40, until the snap-fit mechanism(s) 42 engage. When the modules 14, 16 are attached in this way, the first module 14 surrounds the injector rod sleeve 36 and the front portion 22a of the injector rod 22. The modules 14, 16 are configured to detach from one another in a reverse manner, to once again expose the injector rod sleeve 36 and the front portion 22a of the injector rod 22 for cleaning.

In most circumstances of the device's surgical use, the internal components of the device 10, e.g., the injector rod 22, can be adequately cleaned of accumulated substances as described above. Indeed, in most circumstances, the substances accumulate only on the front-most portions of the internal components, such as the front portion 22a of the injector rod 22, and thus exposing only these portions for cleaning is often adequate.

In other circumstances, however, the substances may also accumulate on those portions of the internal components not exposed by the embodiments above. In the embodiments illustrated in FIGS. 4A-4B, for instance, the substances may accumulate on those portions of the injector rod 22 that are surrounded by the injector rod sleeve 36. Simply detaching the first module 14 from the second module 16 as described above therefore does not sufficiently expose these portions when the injector rod 22 is in the retracted position for cleaning.

Accordingly, FIGS. 5A-5E illustrate embodiments directed to cleaning internal components of the device 10 not sufficiently exposed by detaching the first module 14 from the second module 16. In these embodiments, the second module 16 is configured to, when detached from the first module 14, removably attach to a cleaning module 44. The cleaning module 44 is configured to inject cleaning fluid onto various internal components of the device 10, e.g., the injector rod 22, including those portions not exposed when the injector rod 22 is in the retracted position and when the second module 16 is detached from the first module 14.

More particularly, the first and second modules 14, 16 in these embodiments may be configured to attach and detach in much the same way as described above; that is, via mechanical threads 38 disposed on an external surface of an injector rod sleeve 36 that engage with mechanical threads 40 disposed on an internal surface of the first module 14, and/or via respective portions of one or more snap-fit mechanisms 42. Additionally, though, the injector rod sleeve 36 may be configured to removably attach to the cleaning module 44 when not attached to the first module 14. For example, the injector rod sleeve 36 may further include a cleaning module connector 36a that protrudes from the second module 16 toward the front end 18 of the housing 12 in cantilever fashion. This cleaning module connector 36a is sized and configured to removably attach to the cleaning module 44.

As pictured, the cleaning module 44 includes a syringe 46 filled with a cleaning fluid (e.g., a sterile balanced salt solution) and a tube 48. One end 48a of the tube 48 is configured to attach to the syringe 46. The other end 48b of the tube 48 is configured to pass over the front portion 22a of the injector rod 22 in the retracted position and to attach to the second module 16, e.g., via the cleaning module connector 36a of the injector rod sleeve 36, which is sized and configured for such attachment. With the syringe 46 attached to the second module 16 in this way, cleaning fluid can be injected by the syringe into the injector rod sleeve 36 and onto those internal components of the device 10 not exposed by the detachment of the first module 14.

In some embodiments, the injector rod sleeve 36 has at least one fluid outlet port 36b in a side wall thereof. The fluid outlet port 36b is configured to dispel cleaning fluid injected into the injector rod sleeve 36 and onto the injector rod 22 by the cleaning module 44. As pictured, for example, cleaning fluid flows from the syringe 46, through the tube 48, into the injector rod sleeve 36, onto otherwise unexposed portions of the injector rod 22 and other unexposed internal components of the device 10, and out of the fluid outlet port 36b.

Figure 5E:
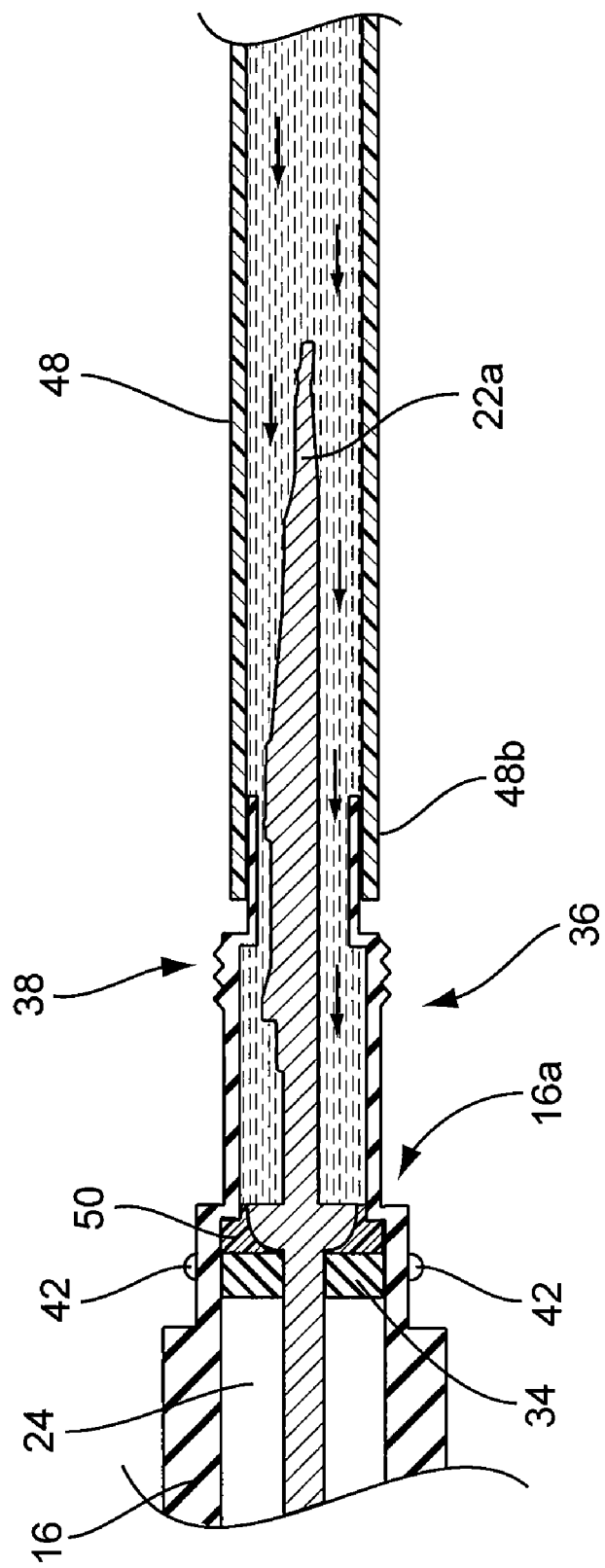

To prevent cleaning fluid injected by the cleaning module 44 from flowing into undesired portions of the device 10, e.g., near the electric drive system 30 at the rear end 20 of the housing 12, various embodiments such as the one illustrated in FIG. 5E include a seal member 50. The seal member 50 may for instance comprise a compression seal made up of an elastomer jacket and a metal channel ring. In the embodiment of FIG. 5E, the seal member 50 is disposed within the passageway 24 near a front end 16a of the second module 16. So disposed, the seal member 50 and the injector rod 22 are configured to engage one another when the rod 22 is in the retracted position. Engaged in this way, the seal member 50 prevents cleaning fluid injected onto the rod 22 from passing beyond the front end 16a of the second module 16 toward the rear end 20 of the housing 12. The seal member 50 thus also, in certain embodiments, facilitates the dispelling of the cleaning fluid out of a fluid outlet port 36b.

Figure 6:
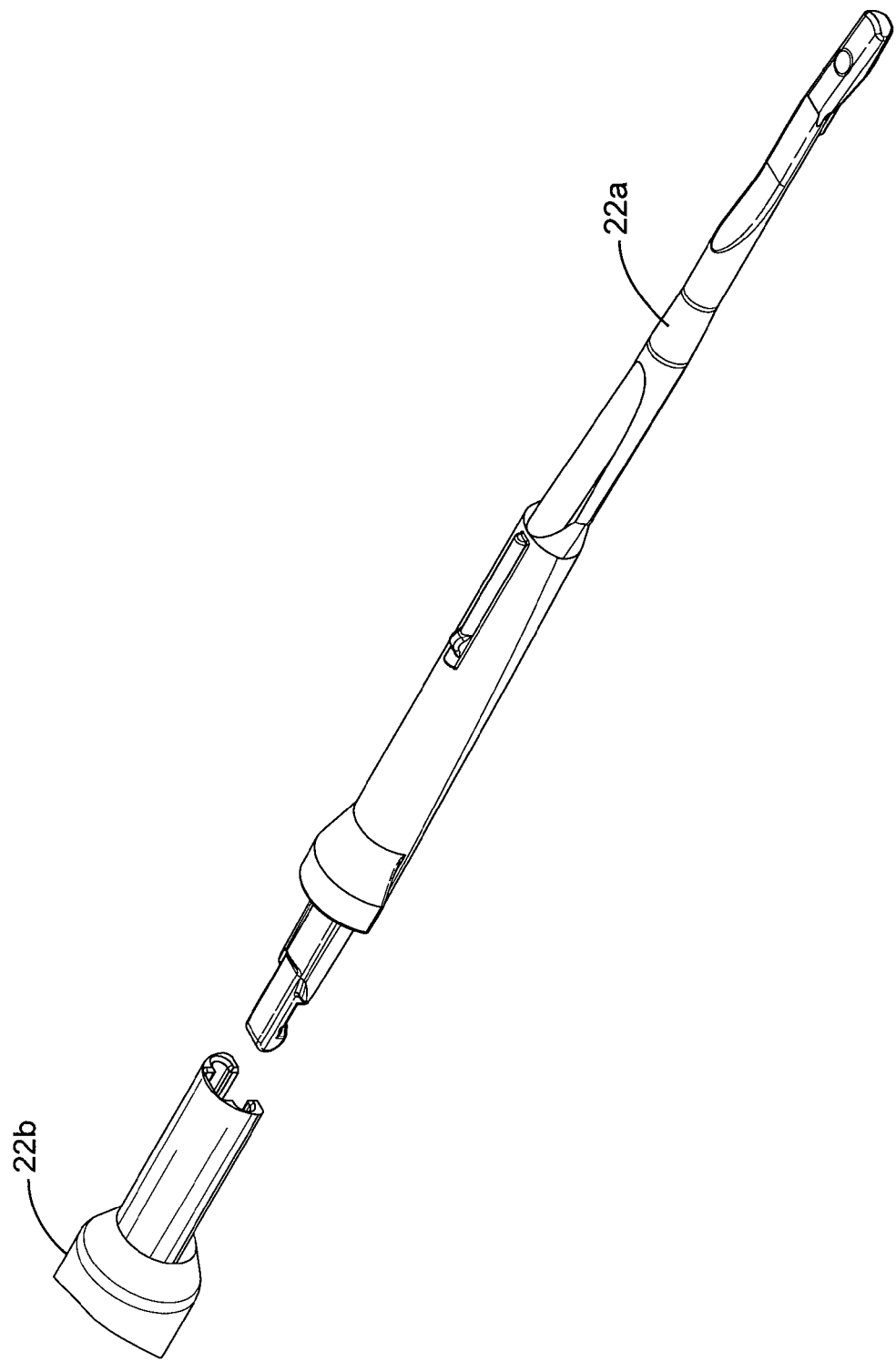
FIG. 6 illustrates an injection rod that includes a removable plunger tip according to some embodiments of the present invention.

Those skilled in the art will appreciate that, although the injector rod 22 was described above for illustrative purposes as comprising a single integral part, the injector rod 22 may comprises two or more parts as shown in FIG. 6. As shown in FIG. 6, the front portion 22a of the injector rod 22 comprises a plunger tip that is configured to removably attach to a remaining portion 22b of the injector rod 22. In some embodiments, the plunger tip may comprise a removable plastic sleeve that snap-fits onto the remaining portion 22b of the rod 22, and may be disposable after use. Furthermore, the end of the plastic sleeve that engages the IOL is more compliant than a bare metallic plunger tip would be, and has a smooth surface finish, thus avoiding damage to the IOL as it is pushed through the lens cartridge module 26 and into the eye. The use of a disposable plastic sleeve may also ease cleaning of the IOL injection device 10 between uses, as fewer portions of the injector rod 22 need by cleaned as described above.

Thus, the preceding description of various embodiments of an intraocular lens injection device was given for purposes of illustration and example. Those skilled in the art will appreciate that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A device for injecting an intraocular lens into an eye, the device comprising:
  a tubular housing comprising a first module at a front end of the housing and a second module posterior to the first module, the first and second modules collectively defining a passageway extending from the second module, through the first module, to the front end of the housing, wherein the first module is configured to accommodate a lens cartridge module at or near the front end of the housing that has an intraocular lens disposed therein, in alignment with said passageway; and
  an injector rod moveable along said passageway over an operating range between a retracted position and an extended position, wherein as the rod moves from the retracted position to the extended position a front portion of the rod that is substantially surrounded by the first module in the retracted position moves into the cartridge module and displaces the intraocular lens therefrom;
  wherein the first module is configured to detach from the second module, to thereby expose the front portion of the rod in the retracted position for cleaning.

2. The device of claim 1, wherein the first module includes a first attachment feature and the second module includes a second attachment feature, the first and second attachment features configured to attach to one another, for surgical use, and to detach from one another, for cleaning.

3. The device of claim 2, wherein the first attachment feature comprises mechanical threads disposed on an interior surface of the first module and the second attachment feature comprises mechanical threads disposed on an exterior surface of the second module.

4. The device of claim 1, wherein the second module includes an injector rod sleeve that protrudes from the second module, toward the front end of the housing, in cantilever fashion and that surrounds at least a portion of the rod longitudinally disposed therein.

5. The device of claim 4, wherein the injector rod sleeve is surrounded by the first module when the first and second modules are attached, and exposed when the first and second modules are detached.

6. The device of claim 4, wherein the first module includes first mechanical threads disposed on an interior surface thereof and wherein the injector rod sleeve includes second mechanical threads disposed on an exterior surface thereof, said first and second mechanical threads configured to removably attach the first and second modules together.

7. The device of claim 1, wherein the front portion of the rod comprises a plunger tip that is configured to removably attach to a remaining portion of the rod.

8. The device of claim 1, wherein the front portion of the rod is integral with a remaining portion of the rod.

9. The device of claim 1, wherein the second module is configured to, when detached from the first module, removably attach to a cleaning module configured to inject cleaning fluid onto said injector rod.

10. The device of claim 9, wherein the second module includes an injector rod sleeve that protrudes from the second module, toward the front end of the housing, in cantilever fashion, that surrounds at least a portion of the rod longitudinally disposed therein, and that is configured to removably attach to the cleaning module.

11. The device of claim 10, wherein the injector rod sleeve has at least one fluid outlet port in a side wall thereof that is configured to dispel cleaning fluid injected into the injector rod sleeve and onto the injector rod by the cleaning module.

12. The device of claim 9, wherein the cleaning module comprises a syringe filled with cleaning fluid and a tube with a first end and a second end, the first end configured to attach to the syringe, and wherein the second module is sized and configured to attach to the second end of said tube.

13. The device of claim 9, wherein the second module includes a seal member disposed within said passageway near a front end of the second module, the seal member and the rod configured to engage one another when the rod is in the retracted position, and to thereby prevent cleaning fluid injected onto the rod by the cleaning module from passing beyond said front end of the second module toward a rear end of the housing.

14. The device of claim 1, wherein the second module houses an electric drive system that includes an electric motor and that is configured to cause longitudinal translation of the injector rod along said passageway over said operating range between the retracted position and the extended position.

* * * * *